United States Patent
Wendel et al.

(10) Patent No.: US 7,201,893 B2
(45) Date of Patent: *Apr. 10, 2007

(54) STABILIZATION OF UV-SENSITIVE ACTIVE INGREDIENTS

(75) Inventors: Volker Wendel, Hamburg (DE); Anja Göppel, Hamburg (DE)

(73) Assignee: Beiersdorf AG, Hamburg (DE)

( * ) Notice: Subject to any disclaimer, the term of this patent is extended or adjusted under 35 U.S.C. 154(b) by 355 days.

This patent is subject to a terminal disclaimer.

(21) Appl. No.: 10/789,750

(22) Filed: Feb. 27, 2004

(65) Prior Publication Data

US 2004/0247539 A1    Dec. 9, 2004

Related U.S. Application Data

(63) Continuation of application No. PCT/EP02/09309, filed on Aug. 21, 2002.

(30) Foreign Application Priority Data

Aug. 29, 2001    (DE)  ................ 101 41 474

(51) Int. Cl.
| | |
|---|---|
| *A61K 8/00* | (2006.01) |
| *A61K 8/04* | (2006.01) |
| *A61K 31/53* | (2006.01) |
| *A61Q 17/00* | (2006.01) |
| *A61Q 17/04* | (2006.01) |
| *A61Q 19/00* | (2006.01) |

(52) U.S. Cl. .................... 424/59; 424/60; 424/400; 424/401; 514/241

(58) Field of Classification Search ............ 424/59, 424/60, 400, 401; 514/241
See application file for complete search history.

(56) References Cited

U.S. PATENT DOCUMENTS

| | | | | |
|---|---|---|---|---|
| 5,980,871 | A * | 11/1999 | Lukenbach et al. ......... | 424/59 |
| 5,993,789 | A | 11/1999 | Bonda et al. | |
| 6,113,931 | A | 9/2000 | Bonda et al. | |
| 6,126,925 | A | 10/2000 | Bonda et al. | |
| 6,129,909 | A | 10/2000 | Bonda et al. | |
| 6,180,091 | B1 | 1/2001 | Bonda et al. | |
| 6,284,916 | B1 | 9/2001 | Bonda et al. | |
| 6,355,230 | B2 * | 3/2002 | Gers-Barlag et al. ......... | 424/59 |
| 6,355,261 | B1 | 3/2002 | Bonda et al. | |
| 6,368,578 | B1 * | 4/2002 | Gers-Barlag et al. ......... | 424/59 |
| 6,403,067 | B1 | 6/2002 | Schamper et al. | |
| 6,440,402 | B1 * | 8/2002 | Gonzalez et al. ............. | 424/59 |
| 6,468,511 | B1 | 10/2002 | Chopra et al. | |
| 6,491,901 | B2 * | 12/2002 | Gers-Barlag et al. ......... | 424/59 |
| 2001/0022966 | A1 | 9/2001 | Gers-Barlag et al. | |
| 2001/0026790 | A1 | 10/2001 | Gers-Barlag et al. | |
| 2002/0164296 | A1 | 11/2002 | Schamper et al. | |
| 2002/0192172 | A1 | 12/2002 | Chopra et al. | |
| 2003/0170284 | A1 | 9/2003 | Dorschner et al. | |

FOREIGN PATENT DOCUMENTS

| | | | |
|---|---|---|---|
| DE | 199 49 825 | A1 | 4/2001 |
| FR | 2 801 201 | A1 | 5/2001 |
| FR | 2 801 206 | A | 5/2001 |
| FR | 2 801 207 | A | 5/2001 |
| FR | 2 801 208 | A | 5/2001 |
| FR | 2 801 209 | A | 5/2001 |
| FR | 2 801 213 | A1 | 5/2001 |
| GB | 660131 | A | 10/1951 |
| WO | WO 02 17873 | A | 3/2002 |

OTHER PUBLICATIONS

"Illinois Researcher Receives Award for Developing a Better Sunscreen," EurekAlert! released Jun. 7, 2001 (http://www.eurekalert.org).
"Beauty is Skin Deep," Household and Personal Products Industry (HAPPI), posted online Sep. 2000 (http//www.happi.com/special/sep002.htm).
International Search Report from corresponding International Application No. PCT/EP02/08577, dated Dec. 20, 2002.
German Search Report dated Mar. 27, 2002 for German Application No. DE 101 41 472.2.
German Search report dated Apr. 12, 2002 for German Application No. DE 101 41 473.0.
Bonda C Et Al: "A New Photostabilizer For Full Spectrum Sunscreens" Cosmetics & Toiletries, Wheaton, IL, US, vol. 115, No. 6, 2000, pp. 37-45.
International Search Report from corresponding International Application No. PCT/EP02/09309 dated Sep. 30, 2003.
International Search Report from corresponding International Application No. PCT/EP02/09374 dated Sep. 30, 2003..

(Continued)

*Primary Examiner*—Shelley A. Dodson
(74) *Attorney, Agent, or Firm*—Greenblum & Bernstein, P.L.C.

(57) ABSTRACT

Cosmetic and dermatological formulations containing at least one UV-sensitive active ingredient have increased UV protection and have the active ingredient stabilized against decomposition through addition of at least one dialkyl naphthalate of the structural formula

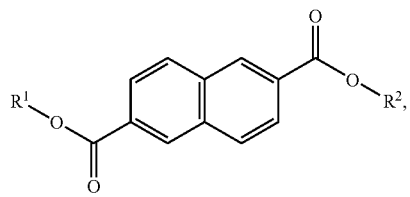

wherein $R^1$ and $R^2$ are selected independently of one another from the group consisting of branched and unbranched alkyl groups having between 6 and 24 carbon atoms, and at least one emulsifier, selected from the group consisting of phosphate and sulphate emulsifiers.

30 Claims, No Drawings

OTHER PUBLICATIONS

International Search Report from corresponding International Application No. PCT/EP02/09375 dated Dec. 10, 2002.
International Search Report from corresponding International Application No. PCT/EP02/09567, dated Sep. 30, 2003.
International Search Report from corresponding International Application No. PCT/EP02/09543 dated Oct. 2, 2003..
International Search Report from corresponding International Application No. PCT/EP02/009310 dated Apr. 12, 2002.
German Search Report for 101 41 474.9 dated Apr. 15, 2002.
German Search Report for 101 41 478.1 dated Apr. 15, 2002.
German Search Report for 101 41 475.7 dated Jul. 19, 2002.

* cited by examiner

US 7,201,893 B2

STABILIZATION OF UV-SENSITIVE ACTIVE INGREDIENTS

CROSS-REFERENCE TO RELATED APPLICATIONS

This is a continuation application of PCT/EP02/09309, filed Aug. 21, 2002, which is incorporated herein by reference in its entirety, and also claims the benefit of German Priority Application No. 101 41 474.9, filed Aug. 29, 2001.

FIELD OF THE INVENTION

The present invention relates to substance combinations for stabilizing UV-sensitive active ingredients, and to cosmetic and dermatological formulations containing UV-sensitive active ingredients stabilized in this way. In particular, it relates to cosmetic and dermatological photoprotective formulations and formulations with UV-sensitive photoprotective filter substances which are stabilized through the use of these substance combinations.

BACKGROUND OF THE INVENTION

The harmful effect of the ultraviolet part of solar radiation on the skin is generally known. The rays have different effects on the skin organ depending on their particular wavelength: so-called UV-C radiation with a wavelength below 290 nm is absorbed by the ozone layer in the earth's atmosphere and therefore is of no physiological importance. By contrast, rays in the range between 290 nm and 320 nm, the so-called UV-B region, cause erythema, simple sunburn or even burns of greater or lesser severity. A maximum for the erythema activity of sunlight is stated as being the relatively narrow range around 308 nm.

Numerous compounds are known for protecting against UV-B radiation, examples thereof being derivatives of 3-benzylidenecamphor, of 4-aminobenzoic acid, of cinnamic acid, of salicylic acid, of benzophenone, and of triazine.

It has long been incorrectly assumed that the long-wave UV-A radiation with a wavelength between 320 nm and 400 nm has only a negligible biological effect. However, it has now been proven by numerous studies that UV-A radiation is far more hazardous than UV-B radiation with regard to the triggering of photodynamic, specifically phototoxic, reactions and chronic changes in the skin. The harmful effect of UV-B radiation can also be further intensified by UV-A radiation.

Thus, it has been proven, inter alia, that even UV-A radiation under entirely normal everyday conditions is sufficient to damage within a short time the collagen and elastin fibers which are of essential importance for the structure and firmness of the skin. This results in chronic photoinduced changes in the skin—the skin "ages" prematurely. The clinical appearance of skin aged by light includes, for example, wrinkles and lines and an irregular, furrowed relief. In addition, the areas affected by photoinduced skin aging may have irregular pigmentation. The formation of brown spots, keratoses and even carcinomas or malignant melanomas is also possible. Skin aged prematurely by everyday exposure to UV is additionally characterized by a lower activity of the Langerhans cells and a slight chronic inflammation.

Approximately 90% of the ultraviolet radiation which reaches the earth consists of UV-A rays. Whereas UV-B radiation varies greatly depending on numerous factors (for example time of year and time of day or latitude), UV-A radiation remains relatively constant from day to day irrespective of seasonal and diurnal or geographic factors. At the same time, most of the UV-A radiation penetrates into the living epidermis, while about 70% of the UV-B rays are retained by the horny layer.

It is therefore of fundamental importance that cosmetic and dermatological photoprotective preparations provide adequate protection both against UV-B and against UV-A radiation.

In general, the light absorption behavior of photoprotective filter substances is very well known and documented, especially since most industrialized countries have positive lists for the use of such substances, which impose very strict standards on the documentation.

However, the concentration in which known photoprotective filter substances present as solids are used is often restricted—in particular in combination with other substances which are to be dissolved. There are thus certain technical difficulties with regard to formulating in achieving relatively high sun protection factors and UV-A protection performance.

Advantageous UV-A filter substances are e.g. dibenzoylmethane derivatives, in particular 4-(tert-butyl)-4'-methoxy-dibenzoylmethane (CAS No. 70356-09-1), which is sold by Givaudan under the name Parsol® 1789 and by Merck under the trade name Eusolex® 9020.

The main disadvantage of all dibenzoylmethane derivatives which absorb in the UV region is a certain instability toward UV radiation, meaning that these components are decomposed under the influence of UV to give inactive products and are no longer available for UV absorption. Preparations of the prior art with a content of these substances therefore expediently also comprise certain UV stabilizers such as, for example, ethylhexyl 2-cyano-3,3-diphenylacrylate (octocrylene) or 4-methylbenzylidene-camphor.

SUMMARY OF THE INVENTION

An object of the present invention was to overcome the disadvantages of the prior art and to arrive in a simple manner at preparations which are distinguished by a high UV, in particular UV-A, protection performance and in which the use of customary UV stabilizers can be dispensed with.

It was surprising and could not have been foreseen by the person skilled in the art that cosmetic and dermatological formulations containing at least one UV-sensitive active ingredient, characterized in that they comprise (a) at least one dialkyl naphthalate which is characterized by the structural formula

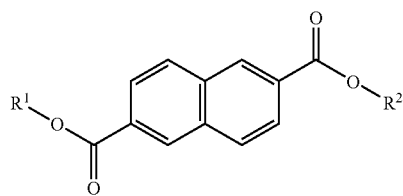

in which $R^1$ and $R^2$, independently of one another, are chosen from the group of branched and unbranched alkyl groups having 6 to 24 carbon atoms, and (b) at least one emulsifier chosen from the group of phosphate and/or sulfate emulsifiers overcome the disadvantages of the prior art.

If the UV-sensitive active ingredient(s) are present in a formulation according to the invention, then they are protected in an excellent manner against the decomposition induced by UV radiation. This is true in particular for dibenzoylmethane derivatives.

DETAILED DESCRIPTION OF THE PREFERRED EMBODIMENTS

The invention therefore also provides for the use of substance combinations which comprise (a) at least one dialkyl naphthalate which is characterized by the structural formula

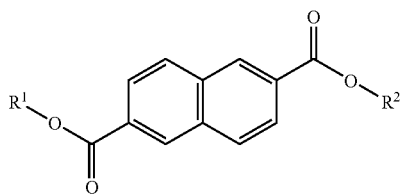

in which $R^1$ and $R^2$, independently of one another, are chosen from the group of branched and unbranched alkyl groups having 6 to 24 carbon atoms, and (b) at least one emulsifier chosen from the group of phosphate and/or sulfate emulsifiers for stabilizing cosmetic or dermatological active ingredients against the decomposition induced by UV radiation.

As well as one or more oil phases, the preparations for the purposes of the present invention can additionally comprise one or more water phases and be present, for example, in the form of W/O, O/W, PIT, W/O/W or O/W/O emulsions. Such emulsions may preferably also be a hydrodispersion.

It was particularly surprising that the use according to the invention stabilizes UV-sensitive active ingredients in O/W emulsions in an excellent manner. The stability of UV-sensitive active ingredients in oil-in-water formulations can be increased considerably through the use according to the invention compared with the prior art.

The preparations according to the invention are entirely satisfactory preparations in every respect which are not restricted to the limited choice of raw materials. Accordingly, they are very particularly suitable for use as bases for preparation forms with diverse application purposes. The preparations according to the invention exhibit very good sensory and cosmetic properties, such as, for example, extensibility on the skin or the ability to absorb into the skin, and are further distinguished by very good photoprotection effectiveness coupled with excellent skincare data.

It was particularly surprising that with the use according to the present invention it is possible to dispense entirely with the use of further UV stabilizers, in particular with the use of ethylhexyl 2-cyano-3,3-diphenylacrylate (octocrylene) or 4-methylbenzylidenecamphor.

Advantageous UV-sensitive active ingredients which are stabilized by the use according to the invention in an excellent manner are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Advantageous for the purposes of the present invention are dialkyl naphthalates in which $R^1$ and/or $R^2$ are branched alkyl groups having 6 to 10 carbon atoms. Very particular preference for the purposes of the present invention is given to diethylhexyl naphthalate, which is obtainable, for example, under the trade name Hallbrite TQ™ from CP Hall or Corapan TQ™ from H&R.

According to the invention, cosmetic or dermatological preparations advantageously comprise 0.001 to 30% by weight, preferably 0.01 to 20% by weight, very particularly preferably 0.5 to 15% by weight, of one or more dialkyl naphthalates.

Phosphate and/or sulfate emulsifiers which are advantageous according to the invention are those which have an HLB value greater than 9.

Advantageous phosphate emulsifiers for the purposes of the present invention are mono-, di- or trialkyl esters of phosphoric acid, which are characterized by the following structure:

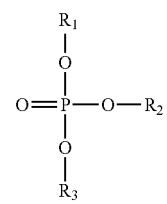

Here, $R_1$, $R_2$ and $R_3$, independently of one another, may be H or branched, optionally alkoxylated, alkyl radicals having 3 to 30, preferably 16 to 24, carbon atoms and/or unbranched, optionally alkoxylated, alkyl radicals having 1 to 30, preferably 16 to 24, carbon atoms.

It is particularly advantageous to use branched and unbranched octadecyl esters as phosphate emulsifier. Such products are sold, for example, by Hoechst AG under the name Hostaphat CG 120.

Also advantageous for the purposes of the present invention is tricetyl phosphate (INCI name: Tricetyl Phosphate, CAS No. 56827-95-3,1-hexadecanol phosphate [3:1]), a triester of phosphoric acid and cetyl alcohol. Tricetyl phosphate corresponds to the following structural formula:

Also advantageous for the purposes of the present invention is cetyl phosphate. Cetyl phosphate is a complex mixture of the esters of phosphoric acid and cetyl alcohol, which corresponds to the general formula $C_{16}H_{35}O_4P$. Cetyl phosphate has the CAS No. 353943-3 and is also referred to as 1-hexadecanol dihydrogenphosphate.

A further phosphate emulsifier which is advantageous according to the invention is Trilaureth-4 Phosphate. Trilaureth-4 Phosphate is the INCI name for the triester of polyethylene (200) lauryl ether and phosphoric acid. Trilaureth-4 phosphate is obtainable, for example, under the trade name Hostaphat KL 340 N from Hoechst AG.

Also advantageous for the purposes of the present invention is Trilaneth-4 Phosphate. Trilaneth-4 Phosphate is the INCI name for a triester of phosphoric acid and ethoxylated wool wax alcohols (RD No. 977058-52-8).

A further phosphate emulsifier which is advantageous according to the invention is that with the INCI name Triceteareth-4 Phosphate, which is available under the trade name Hostaphat KW 340 N from Hoechst AG.

Also advantageous for the purposes of the present invention is the phosphate emulsifier with the INCI name Trioleth-8 Phosphate, which is available under the trade name Hostaphat KO 380 from Hoechst AG.

A further phosphate emulsifier which is advantageous according to the invention is that with the INCI name Trioleyl Phosphate, which is available under the trade name Hostaphat KO 300 from Hoechst AG.

An advantageous sulfate emulsifier for the purposes of the present invention is sodium ceteary1 sulfate (also: sodium cetylstearyl sulfate), and the corresponding potassium or DEA salts. Sodium ceteary1 sulfate which is advantageous according to the invention is available in various mixtures and also as individual raw material from Henkel KGaA under the trade names Lanette N, Lanette E and Emulgade F.

According to the invention, cosmetic or dermatological preparations advantageously comprise 0.01 to 10% by weight, preferably 0.1 to 6% by weight, of one or more phosphate and/or sulfate emulsifiers.

It is also advantageous for the purposes of the present invention to choose the weight ratio of the phosphate and/or sulfate emulsifier (one or more compounds) to the alkyl naphthalate (one or more compounds) from the range from 1:1 to 1:60, in particular from 1:2 to 1:30.

The cosmetic or dermatological photoprotection formulations according to the invention can have the customary composition and be used for cosmetic or dermatological photoprotection, in addition for the treatment, care and cleansing of the skin and/or of the hair and as a make-up product in decorative cosmetics.

Depending on their formulation, cosmetic or topical dermatological compositions for the purposes of the present invention may be used, for example, as skin protection cream, cleansing milk, day or night cream etc. It is in some cases possible and advantageous to use the compositions according to the invention as a basis for pharmaceutical formulations.

For use, the cosmetic and dermatological preparations are applied to the skin and/or the hair in a sufficient amount in the manner customary for cosmetics.

The cosmetic and dermatological preparations according to the invention can comprise cosmetic auxiliaries as are customarily used in such preparations, e.g. preservatives, preservation helpers, bactericides, perfumes, substances to prevent foaming, dyes, pigments which have a coloring action, thickeners, moisturizing and/or humectant substances, fillers which improve the feel of the skin, fats, oils, waxes or other customary constituents of a cosmetic or dermatological formulation, such as alcohols, polyols, polymers, foam stabilizers, electrolytes, organic solvents or silicone derivatives.

Advantageous preservatives for the purposes of the present invention are, for example, formaldehyde donors (such as e.g. DMDM hydantoin, which is available, for example, under the trade name Glydant™ from Lonza), iodopropylbutylcarbamates (e.g. those available under the trade names Glycacil-L, Glycacil-S from Lonza, and/or Dekaben LMB from Jan Dekker), parabens (i.e. p-hydroxybenzoic alkyl esters, such as methyl-, ethyl-, propyl- and/or butylparaben), phenoxyethanol, ethanol, benzoic acid and the like. According to the invention, the preservative system usually also advantageously includes preservation helpers, such as, for example, octoxyglycerol, glycine soya etc. as well.

Particularly advantageous preparations are also obtained when antioxidants are used as additives or active ingredients. According to the invention, the preparations advantageously comprise one or more antioxidants. Favorable, but nevertheless optional antioxidants which may be used are all antioxidants customary or suitable for cosmetic and/or dermatological applications.

For the purposes of the present invention, it may be particularly advantageous to use water-soluble antioxidants, such as, for example, vitamins, e.g. ascorbic acid and derivatives thereof, and D-biotin, natural and/or synthetic isoflavonoids, alpha-glucosylrutin, panthenol, aloe vera.

Advantageous lipophilic active ingredients which are likewise stabilized in an excellent manner through the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{c_{n-octanol}}{c_{water}}$$

It is advantageous for the purposes of the present invention to choose the lipophilic active ingredients from the group of ubiquinones and plastoquinones. For the purposes of the present invention, coenzyme Q10, which has a log P value of about 15, is very particularly advantageous.

Further lipophilic active ingredients which are advantageous according to the invention are retinoids (vitamin A acid and/or derivatives thereof) or vitamin A and/or derivatives thereof. The group of retinoids advantageous according to the invention is defined as including all cosmetically and/or pharmaceutically acceptable retinoids, including retinol and its esters, retinal and also retinoic acid (vitamin A acid) and esters thereof. For the purposes of the present invention, retinol (with a log P value of about 7) and retinyl palmitate (with a log P value of about 13) are particularly advantageous.

Further lipophilic active ingredients advantageous according to the invention are carotenoids. For the purposes of the present invention, 1-carotene, for example, which has a log P value of 15, is particularly advantageous.

Further lipophilic active ingredients advantageous according to the invention are:

lipoic acid and derivatives,
vitamin E and derivatives,
vitamin F,
dioic acid [8-hexadecene-1,16-dicarboxylic acid (CAS number 20701-68-2)]

It is particularly advantageous when the cosmetic preparations according to the present invention comprise cosmetic or dermatological active ingredients, preferred active ingredients being antioxidants which can protect the skin against oxidative stress.

Advantageous further active ingredients are natural active ingredients and/or derivatives thereof, such as e.g. phytoene, carnitine, carnosine, creatine, taurine and/or β-alanine.

The amount of antioxidants and/or active ingredients (one or more compounds) in the preparations is preferably 0.001 to 30% by weight, particularly preferably 0.05 to 20% by weight, in particular 0.1 to 10% by weight, based on the total weight of the preparation.

Formulations according to the invention, which comprise e.g. known antiwrinkle active ingredients, such as flavone glycosides (in particular α-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

The water phase of the preparations according to the invention can advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, and in particular one or more thickeners which may advantageously be chosen from the group consisting of silicon dioxide, aluminum silicates, polysaccharides or derivatives thereof, e.g. hyaluronic acid, xanthan gum, hydroxypropylmethylcellulose, particularly advantageously from the group of polyacrylates, preferably a polyacrylate from the group of so-called carbopols, for example Carbopol 980, 981, 1382, 2984, 5984, in each case individually or in combination. Moisturizers can also preferably be used.

Also advantageous are copolymers of $C_{10-30}$-alkyl acrylates and one or more monomers of acrylic acid, of methacrylic acid or esters thereof which are crosslinked with an allyl ether of sucrose or an allyl ether of pentaerythritol.

Compounds which bear the INCI name "Acrylates/$C_{10-30}$ Alkyl Acrylate Crosspolymer" are advantageous. Those available under the trade names Pemulen TR1 and Pemulen TR2 from B. F. Goodrich Company are particularly advantageous.

Compounds which bear the INCI name Ammonium Acryloyldimethyltaurate/Vinylpyrrolidone copolymers are advantageous.

According to the invention, the Ammonium Acryloyldimethyltaurate/Vinylpyrrolidone copolymers advantageously have the empirical formula $[C_7H_{16}N_2SO_4]_n$ $[C_6H_9NO]_m$, corresponding to a statistical structure as follows

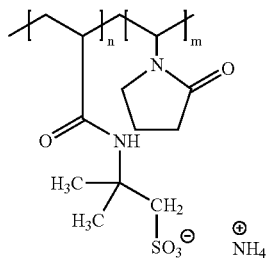

Preferred species for the purposes of the present invention are listed in Chemical Abstracts under the Registry numbers 58374-69-9, 13162-05-5 and 88-12-0 and are available under the trade name Aristoflex® AVC from Clariant GmbH.

Also advantageous are copolymers/crosspolymers comprising Acryloyldimethyl Taurate, such as, for example, Simugel® EG or Simugel® EG from Seppic S.A.

Moisturizers is the term used for substances or mixtures of substances which, following application or distribution on the surface of the skin, confer on cosmetic or dermatological preparations the property of reducing the moisture loss by the horny layer (also called transepidermal water loss (TEWL)) and/or have a positive influence on the hydration of the horny layer.

Advantageous moisturizers for the purposes of the present invention are, for example, glycerol, lactic acid and/or lactates, in particular sodium lactate, butylene glycol, propylene glycol, biosaccharide gum-1, glycine soya, ethylhexyloxyglycerol, pyrrolidonecarboxylic acid and urea. In addition, it is particularly advantageous to use polymeric moisturizers from the group of water-soluble and/or water-swellable and/or water-gellable polysaccharides. Particularly advantageous are, for example, hyaluronic acid, chitosan and/or a fucose rich polysaccharide which is listed in Chemical Abstracts under the Registry number 178463-23-5 and is available, for example, under the name Fucogel®1000 from SOLABIA S.A.

The cosmetic or dermatological preparations according to the invention can also advantageously, but not necessarily, comprise fillers which, for example, further improve the sensory and cosmetic properties of the formulations and, for example, bring about or intensify a velvety or silky feel on the skin. Advantageous fillers for the purposes of the present invention are starch and starch derivatives (such as e.g. tapioca starch, distarch phosphate, aluminum or sodium starch octenylsuccinate and the like), pigments which primarily have neither a UV filter effect nor a coloring effect (such as e.g. boron nitride etc.) and/or Aerosils® (CAS No. 7631-86-9).

The oil phase of the formulations according to the invention is advantageously chosen from the group of polar oils, for example from the group of lecithins and of fatty acid triglycerides, namely the triglycerol esters of saturated and/or unsaturated, branched and/or unbranched alkanecarboxylic acids with a chain length from 8 to 24, in particular 12 to 18, carbon atoms. The fatty acid triglycerides can, for example, advantageously be chosen from the group of synthetic, semisynthetic and natural oils, such as e.g. cocoglyceride, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like.

Also advantageous according to the invention are e.g. natural waxes of animal and vegetable origin, such as, for example beeswax and other insect waxes, and berry wax, shea butter and/or lanolin (wool wax).

Further advantageous polar oil components for the purposes of the present invention may also be chosen from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length from 3 to 30 carbon atoms. Such ester oils can then advantageously be chosen from the group consisting of octyl palmitate, octyl cocoate, octyl isostearate, octyldodeceyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as e.g. jojoba oil.

The oil phase can also advantageously be chosen from the group of dialkyl ethers and dialkyl carbonates, advantageous examples being dicaprylyl ether (Cetiol OE) and/or dicaprylyl carbonate, for example that available under the trade name Cetiol CC from Cognis.

It is also preferred the oil component(s) from the group consisting of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethylisosorbide. It is particularly advantageous if the oil phase of the formulations according to the invention has a content of $C_{12-15}$-alkyl benzoate or consists entirely of this.

Advantageous oil components are also e.g. butyloctyl salicylate (for example that available under the trade name Hallbrite BHB from CP Hall), hexadecyl benzoate and butyloctyl benzoate and mixtures thereof (Hallstar AB).

Any desired mixtures of such oil and wax components can be used advantageously for the purposes of the present invention.

In addition, the oil phase can likewise advantageously also comprise nonpolar oils, for example those chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are linked in a chain-like and/or network-like manner via oxygen atoms, and the remaining valences of the silicon are saturated by hydrocarbon radicals (in most cases methyl, less often ethyl, propyl, phenyl groups etc.). Systematically, the silicone oils are referred to as polyorganosiloxanes. The methyl-substituted polyorganosiloxanes, which represent the most significant compounds of this group in terms of number and are characterized by the following structural formula

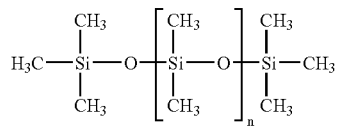

are also referred to as polydimethylsiloxane or Dimethicone (INCI). There are dimethicones with various chain lengths and with various molecular weights.

For the purposes of the present invention, particularly advantageous polyorganosiloxanes are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane or decamethylcyclopentasiloxane), which are also referred to as Cyclomethicones in accordance with INCI, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt. However, for the purposes of the present invention, other silicone oils can also advantageously be used, for example cetyldimethicone, hexamethylcyclotrisiloxane, polydimethylsiloxane, poly(methylphenylsiloxane).

For the purposes of the present invention, it is also advantageous to create cosmetic and dermatological preparations whose main purpose is not protection against sunlight, but which nevertheless contain a content of further UV protection substances. Thus, for example, UV-A and/or UV-B filter substances are usually incorporated into day creams or make-up products. UV protection substances, like antioxidants and, if desired, preservatives, represent effective protection of the preparations themselves against decay. Also favorable are cosmetic and dermatological preparations which are in the form of a sunscreen composition.

Accordingly, the preparations within the meaning of the present invention preferably comprise at least one further UV-A, UV-B and/or broadband filter substance. The formulations may, but do not necessarily, optionally also comprise one or more organic and/or inorganic pigments as UV filter substances, which may be present in the water phase and/or the oil phase.

In addition, the preparations according to the invention can advantageously also be in the form of so-called oil-free cosmetic or dermatological emulsions, which comprise a water phase and at least one UV filter substance which is liquid at room temperature and/or one or more silicone derivatives as the further phase. Oil-free formulations for the purposes of the present invention may advantageously also comprise further lipophilic components—such as, for example, lipophilic active ingredients.

Particularly advantageous UV filter substances which are liquid at room temperature for the purposes of the present invention are homomenthyl salicylate (INCI: Homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Octyl Salicylate) and esters of cinnamic acid, preferably 4-methoxycinnamic 2-ethylhexyl ester (2-ethylhexyl 4-methoxycinnamate, INCI: Octyl Methoxycinnamate) and 4-methoxycinnamic isopentyl ester (isopentyl 4-methoxycinnamate, INCI: Isoamyl p-Methoxycinnamate).

Preferred inorganic pigments are metal oxides and/or other metal compounds which are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

The pigments can advantageously be used for the purposes of the present invention also in the form of commercially available oily or aqueous predispersions. Dispersion auxiliaries and/or solubility promoters may advantageously be added to these predispersions.

The pigments may, according to the invention, advantageously be surface-treated ("coated"), the intention being, for example, to form or retain a hydrophilic, amphiphilic or hydrophobic character. This surface treatment can consist in providing the pigments with a thin hydrophilic and/or hydrophobic inorganic and/or organic layer by methods known per se. The various surface coatings for the purposes of the present invention may also comprise water.

Inorganic surface coatings for the purposes of the present invention may consist of aluminum oxide ($Al_2O_3$), aluminum hydroxide $Al(OH)_3$, or aluminum oxide hydrate (also: alumina, CAS No.: 1333-84-2), sodium hexametaphosphate ($(NaPO_3)_6$), sodium metaphosphate ($(NaPO_3)_n$), silicon dioxide ($SiO_2$) (also: silica, CAS No.: 7631-86-9), or iron oxide ($Fe_2O_3$). These inorganic surface coatings may exist on their own, in combination and/or in combination with organic coating materials.

Organic surface coatings for the purposes of the present invention may consist of vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of from 200 to 350 dimethylsiloxane units and silica gel) or alginic acid. These organic surface coatings may exist on their own, in combination and/or in combination with inorganic coating materials.

Zinc oxide particles and predispersions of zinc oxide particles which are suitable according to the invention are available under the following trade names from the companies listed:

| Trade name | Coating | Manufacturer |
| --- | --- | --- |
| Z-Cote HP1 | 2% dimethicone | BASF |
| Z-Cote | / | BASF |
| ZnO NDM | 5% dimethicone | H&R |
| ZnO Neutral | / | H&R |
| MZ 505 M | 5% methicone | Tayca Corp. |

Suitable titanium dioxide particles and predispersions of titanium dioxide particles are available under the following trade names from the companies listed:

| Trade name | Coating | Manufacturer |
| --- | --- | --- |
| MT-100TV | aluminum hydroxide/stearic acid | Tayca Corporation |
| MT-100Z | aluminum hydroxide/stearic acid | Tayca Corporation |
| Eusolex T-2000 | alumina/simethicone | Merck KgaA |
| Titanium dioxide T805 (Uvinul $TiO_2$) | octyltrimethylsilane | Degussa |
| Tioveil AQ 10PG | alumina/silica | Solaveil/Uniquema |

Further advantageous pigments are latex particles. Latex particles which are advantageous according to the invention are those described in the following specifications: U.S. Pat. No. 5,663,213 and EP 0 761 201. Particularly advantageous latex particles are those which are formed from water and styrene/acrylate copolymers and are available, for example, under the trade name "Alliance SunSphere" from Rohm & Haas.

Advantageous further UV filter substances for the purposes of the present invention are sulfonated, water-soluble UV filters, such as, for example, phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic bis-sodium salt with the INCI name Bisimidazylate (CAS No.: 180898-37-7), which is available, for example, under the trade name Neo Heliopan AP from Haarmann & Reimer;

salts of 2-phenylbenzimidazole-5-sulfonic acid, such as its sodium, potassium or its triethanolammonium salt, and the sulfonic acid itself with the INCI name Phenylbenzimidazole Sulfonic Acid (CAS No. 27503-81-7), which is available, for example, under the trade name Eusolex 232 from Merck or under Neo Heliopan Hydro from Haarmann & Reimer;

1,4-di(2-oxo-10-sulfo-3-bornylidenemethyl)benzene (also: 3,3'-(1,4-phenylene-dimethylene)bis(7,7-dimethyl-2-oxobicyclo[2.2.1]hept-1-ylmethane sulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephtalidene Dicamphor Sulfonic Acid (CAS No.: 90457-82-2) and is available, for example, under the trade name Mexoryl SX from Chimex;

sulfonic acid derivatives of 3-benzylidenecamphor, such as e.g. 4-(2-oxo-3-bornylidenemethyl)benzenesulfonic acid, 2-methyl-5-(2-oxo-3-bornylidene-methyl)sulfonic acid and salts thereof.

Advantageous UV filter substances for the purposes of the present invention are also so-called broadband filters, i.e. filter substances which absorb both UV-A- and also UV-B-radiation.

Advantageous broadband filters or UV-B filter substances are, for example, triazine derivatives, such as e.g.

2,4-bis{[4-(2-ethylhexyloxy)-2-hydroxlphenyl}-6-(4-methoxyphenyl)-1,3,5-triazine (INCI: Methylene Bis-Benzotriazolemethylbutylphenol), which is available under the trade name Tinosorb® S from CIBA-Chemikalien GmbH;

dioctylbutylamidotriazone (INCI: Diethylhexylbutamidotriazone), which is available under the trade name UVASORB HEB from Sigma 3V;

tris(2-ethylhexyl)4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

An advantageous broadband filter for the purposes of the present invention is also 2,2'-methylenebis(6-(2H-benzotriazol-2-yl)-4-(1,1,3,3-tetramethylbutyl)phenol) (INCI: Bisoctyltriazole), which is available under the trade name Tinosorb® M from CIBA-Chemikalien GmbH.

An advantageous broadband filter for the purposes of the present invention is also 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) with the INCI name Drometrizole Trisiloxane.

The further UV filter substances may be oil-soluble. Advantageous oil-soluble filter substances are e.g.:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate amyl 4-(dimethylamino) benzoate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bound to polymers.

A further photoprotective filter substance to be used advantageously according to the invention is ethylhexyl 2-cyano-3,3-diphenyl acrylate (Octocrylene), which is available from BASF under the name Uvinul® N 539.

Particularly advantageous preparations for the purposes of the present invention, which may be characterized by a high or very high UV-A protection, comprise, as well as the filter substance(s) according to the invention, preferably also further UV-A and/or broadband filters, in particular dibenzoylmethane derivatives [for example 4-(tert-butyl)-4'-methoxydibenzoylmethane] and/or 2,4-bis{[4-(2-ethylhexyloxy)-2-hydroxylphenyl}-6-(4-methoxyphenyl)-1,3,5-triazine, in each case individually or in any combinations with one another.

The list of UV filters specified which can be used for the purposes of the present invention is not of course intended to be limiting.

Advantageously, the preparations according to the invention comprise the substances which absorb UV radiation in the UV-A and/or UV-B region in a total amount of e.g. 0.1% by weight to 30% by weight, preferably 0.5 to 20% by weight, in particular 1.0 to 15.0% by weight, in each case based on the total weight of the preparations, in order to provide cosmetic preparations which protect the hair and/or the skin from the entire range of ultraviolet radiation.

In addition, it may in some instances be advantageous to incorporate film formers into the cosmetic or dermatological preparations according to the invention, for example in order to improve the water resistance of the preparations or to increase the UV protection performance (UV-A and/or UV-B boosting). Water-soluble or dispersible and also fat-soluble film formers are suitable, in each case individually or in combination with one another.

Advantageous water-soluble or dispersible film formers are e.g. polyurethanes (e.g the Avalure® grades from Goodrich), dimethicone copolyol polyacrylate (Silsoft Surface® from Witco Organo Silicones Group), PVP/VA (VA=vinyl acetate) copolymer (Luviscol VA 64 Powder from BASF) etc.

Advantageous fat-soluble film formers are e.g. the film formers from the group of polymers based on polyvinylpyrrolidone (PVP)

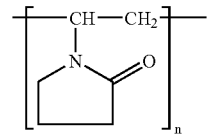

Particular preference is given to copolymers of polyvinylpyrrolidone, for example the PVP hexadecene copolymer and the PVP eicosene copolymer, which are available under the trade names Antaron V216 and Antaron V220 from GAF Chemicals Cooperation and also tricontayl PVP and the like.

The examples below serve to illustrate the present invention without limiting it. The numerical values in the examples are percentages by weight, based on the total weight of the particular preparations.

EXAMPLES

1. O/W Sunscreen Emulsions

|  | 1 | 2 | 3 | 4 | 5 | 6 | 7 |
|---|---|---|---|---|---|---|---|
| Glycerol monostearate SE | 0.50 | 1.00 | 3.00 |  |  | 1.50 |  |
| Glyceryl stearate citrate | 2.00 |  |  | 1.00 | 1.00 |  | 2.50 |
| Stearic acid |  | 3.00 |  | 2.00 |  |  |  |
| PEG-40 stearate | 0.50 |  |  |  |  | 2.00 |  |
| PEG-100 stearate |  | 1.50 |  |  | 3.00 |  |  |
| Cetyl phosphate | 0.50 | 0.75 |  |  | 1.00 |  |  |
| Trilaureth-4 phosphate |  |  | 2.00 | 1.00 |  |  | 2.50 |
| Cetearyl sulfate | 1.00 |  |  | 0.25 | 1.00 | 2.50 |  |
| Stearyl alcohol |  |  | 3.00 |  |  | 2.00 | 0.50 |
| Cetyl alcohol | 2.50 | 1.00 |  | 1.50 | 0.50 |  | 2.00 |
| Ethylhexyl methoxycinnamate |  |  |  |  | 6.00 |  | 8.00 |
| Anisotriazine |  | 1.50 |  |  | 2.50 |  | 2.50 |
| Butylmethoxydibenzoylmethane | 3.00 | 3.00 | 2.00 |  |  | 0.5 | 1.50 |
| Bisimidazylate |  |  | 0.50 |  | 1.00 | 1.70 | 0.30 |
| Ethylhexyltriazone | 4.00 |  | 3.00 |  | 4.00 | 2.00 |  |
| Octocrylene | 10.0 | 4.00 |  |  |  | 10.00 | 2.50 |
| Diethylhexylbutamidotriazone | 1.00 |  |  |  | 1.00 | 1.00 |  |
| Phenylbenzimidazolesulfonic acid | 0.50 |  |  |  |  |  |  |
| Bisoctyltriazole | 2.00 |  | 0.50 |  | 2.50 |  |  |
| Benzophenone-3 |  |  |  |  |  |  |  |
| Homosalate |  | 2.00 |  |  |  | 5.00 |  |
| Ethylhexyl salicylate |  |  | 3.00 |  |  | 4.00 | 5.00 |
| Drometrizole trisiloxane |  |  | 0.5 |  |  | 1.00 |  |
| Terephthalidenedicamphorsulfonic acid |  | 1.50 |  |  | 1.00 | 0.50 |  |
| Diethylhexyl 2,6-naphthalate | 10.0 | 4.80 | 7.00 | 9.50 | 6.70 | 5.50 | 8.00 |
| Titanium dioxide MT-100Z | 1.00 |  | 3.00 |  |  | 2.00 |  |
| Z-Cote HP1 |  |  | 1.50 |  |  |  | 3.00 |
| C12–15 alkylbenzoate |  | 2.50 |  |  | 4.00 |  | 5.00 |
| Dicaprylyl ether |  |  | 3.50 |  | 2.00 |  |  |

-continued

|  | 1 | 2 | 3 | 4 | 5 | 6 | 7 |
|---|---|---|---|---|---|---|---|
| Butylene glycol dicaprylate/Dicaprate | 5.00 |  |  | 6.00 |  |  |  |
| Dicaprylyl carbonate |  | 6.00 |  |  |  |  | 2.00 |
| Dimethicone |  | 0.50 | 1.00 |  | 2.00 |  |  |
| Dibutyl adipate |  |  |  | 3.00 |  |  |  |
| Coco caprylate/caprate |  | 4.50 |  |  | 5.00 |  |  |
| Cyclomethicone | 2.00 |  |  | 0.50 | 3.00 |  | 0.50 |
| Shea butter |  | 2.00 |  |  |  |  | 0.50 |
| PVP hexadecene copolymer | 0.50 |  |  | 0.50 | 1.00 |  | 1.00 |
| Tricontanyl PVP |  | 0.50 | 1.00 |  |  |  | 1.00 |
| Glycerol | 3.00 | 7.50 |  | 7.50 | 5.00 |  | 2.50 |
| Xanthan gum | 0.15 |  | 0.05 |  |  |  | 0.30 |
| Sodium carbomer |  | 0.20 | 0.10 | 0.20 |  |  |  |
| Vitamin E | 0.50 |  | 0.25 |  | 0.75 | 0.55 | 1.00 |
| Vitamin A |  | 0.15 |  |  |  |  |  |
| Fucogel ® 1000 |  |  | 1.50 | 3.00 |  | 7.00 |  |
| Polyurethane |  |  |  |  |  | 0.75 |  |
| Styrene/acrylate copolymer | 0.80 |  |  |  |  |  | 1.00 |
| DMDM hydantoin |  | 0.60 | 0.40 | 0.20 |  |  |  |
| Konkaben LMB ® |  |  |  | 0.18 | 0.20 |  | 0.15 |
| EDTA | 0.20 |  | 0.75 |  | 0.35 | 0.15 |  |
| Methylparaben | 0.15 |  | 0.25 |  | 0.50 |  |  |
| Phenoxyethanol | 1.00 | 0.40 |  | 0.40 | 0.50 | 0.40 | 0.60 |
| Ethanol |  | 2.00 | 1.50 |  | 3.00 |  | 1.00 |
| Perfume | 0.20 |  | 0.20 |  | 0.20 | 0.20 | 0.20 |
| Water | ad 100 | ad 100 | ad 100 | ad 100 | ad 100 | ad 100 | ad 100 |

2. Hydrodispersions with a Low Emulsifier Content

|  | 1 | 2 | 3 | 4 | 5 |
|---|---|---|---|---|---|
| PEG-40 stearate | 0.50 |  |  |  |  |
| Cetyl alcohol |  |  | 1.00 |  |  |
| Sodium carbomer |  | 0.20 |  | 0.30 |  |
| Acrylates/C10–30 alkyl acrylate crosspolymer | 0.50 |  | 0.40 | 0.10 | 0.10 |
| Xanthan gum |  | 0.30 | 0.15 |  | 0.50 |
| Aristoflex ® AVC | 0.50 |  |  |  |  |
| Cetearyl sulfate |  | 1.00 | 0.35 | 0.20 |  |
| Cetyl phosphate | 0.25 |  | 0.10 |  | 0.35 |
| Ethylhexyl methoxycinnamate |  |  |  | 5.00 | 8.00 |
| Anisotriazine |  | 1.50 |  | 2.00 | 2.50 |
| Butylmethoxydibenzoylmethane |  | 0.50 |  | 3.00 |  |
| Bisimidazylate |  | 1.80 |  | 2.00 | 3.00 |
| Ethylhexyltriazone |  |  | 3.00 | 4.00 |  |
| 4-Methylbenzylidene-camphor |  |  |  |  |  |
| Octocrylene |  | 4.00 | 3.90 |  | 2.50 |
| Diethyhexylbutamidotriazone |  |  |  | 2.00 |  |
| Phenylbenzimidazole-sulfonic acid |  |  |  |  | 3.00 |
| Bisoctyltriazole |  | 0.50 |  |  | 0.80 |
| Drometrizole trisiloxane |  |  | 1.00 |  | 1.50 |
| Terephthalidene-dicamphorsulfonic acid |  | 0.50 |  |  | 1.00 |
| Diethylhexyl 2,6-naphthalate | 5.00 | 8.00 | 7.20 | 5.50 | 15.00 |
| Titanium dioxide MT-100TV |  | 3.00 | 2.00 |  | 1.00 |
| Zinc oxide NDM |  |  | 1.00 |  |  |
| C12–15 alkyl benzoate | 2.00 | 2.50 |  |  |  |
| Octyldodecanol |  | 4.00 | 5.00 |  |  |
| Butylene glycol dicaprylate/dicaprate | 4.00 |  | 2.00 | 6.00 |  |
| Dicaprylyl carbonate |  | 2.00 | 6.00 |  |  |
| Isohexadecene | 3.00 |  |  |  |  |
| Dimethicone |  | 0.50 | 1.00 |  |  |
| Phenyltrimethicone | 2.00 |  |  | 0.50 | 2.00 |

-continued

|  | 1 | 2 | 3 | 4 | 5 |
|---|---|---|---|---|---|
| Shea butter |  | 2.00 |  |  |  |
| PVP hexadecene copolymer | 0.50 |  |  | 0.50 | 1.00 |
| Tricontanyl PVP | 0.50 |  | 1.00 |  |  |
| Ethylhexylglycerol |  |  | 1.00 |  | 0.50 |
| Glycerol | 3.00 | 7.50 |  | 7.50 | 2.50 |
| Glycine soya |  |  | 1.50 |  |  |
| Vitamin E | 0.50 |  | 0.25 |  | 1.00 |
| Ascorbyl palmitate |  | 0.50 |  | 2.00 | 0.50 |
| α-Glucosylrutin |  |  | 0.20 |  |  |
| DMDM hydantoin |  | 0.60 | 0.40 | 0.20 |  |
| Konkaben LMB ® | 0.20 |  |  |  |  |
| Octoxyglycerol |  | 0.25 |  |  | 1.00 |
| EDTA | 0.15 | 0.05 | 0.50 |  |  |
| Iminodisuccinic acid |  |  |  | 0.25 |  |
| Glycine soya |  |  | 0.50 |  | 1.50 |
| Methylparaben | 0.50 |  | 0.25 | 0.15 |  |
| Phenoxyethanol | 0.50 | 0.40 |  | 1.00 |  |
| Ethanol | 3.00 | 2.00 | 1.50 |  | 7.00 |
| Perfume | 0.20 | 0.20 | 0.20 |  |  |
| Water | ad 100 | ad 100 | ad 100 | ad 100 | ad 100 |

3. W/O Sunscreen Emulsions

|  | 1 | 2 | 3 | 4 | 5 |
|---|---|---|---|---|---|
| Cetyldimethicone copolyol |  | 2.50 |  | 4.00 |  |
| Polyglyceryl-2 dipolyhydroxystearate | 5.00 | 2.50 |  |  | 4.50 |
| PEG-30 dipolyhydroxystearate |  |  |  | 5.00 | 3.00 |
| Laurylmethicone copolyol |  |  |  | 2.00 | 1.50 |
| Cetearyl sulfate | 0.15 | 0.25 | 2.00 |  |  |
| Trilaureth-4 phosphate |  | 0.10 |  | 1.00 | 0.75 |

-continued

|  | 1 | 2 | 3 | 4 | 5 |
|---|---|---|---|---|---|
| Ethylhexyl methoxy-cinnamate |  | 8.00 |  | 5.00 |  |
| Anisotriazine | 2.00 | 2.50 |  | 2.00 |  |
| Butylmethoxydibenzoyl-methane | 0.50 | 3.00 | 2.00 |  | 0.50 |
| Bisimidazylate | 0.50 |  |  | 2.00 |  |
| Ethylhexyltriazone |  |  | 3.00 | 4.00 | 1.50 |
| 4-Methylbenzylidene-camphor |  | 2.00 |  | 4.00 |  |
| Octocrylene |  | 2.50 | 3.90 |  | 10.00 |
| Diethyhexylbutamido-triazone | 1.00 |  |  | 2.00 |  |
| Phenylbenzimidazole-sulfonic acid | 0.50 |  | 0.50 | 3.00 |  |
| Bisoctyltriazole |  |  | 2.00 | 0.50 |  |
| Drometrizole trisiloxane |  | 1.00 |  |  | 4.50 |
| Terephthalidene-dicamphorsulfonic acid |  |  | 1.00 |  | 0.50 |
| Diethylhexyl 2,6-naphthalate | 7.50 | 5.50 | 3.50 | 8.80 | 9.70 |
| Titanium dioxide T805 |  | 2.00 | 1.50 |  |  |
| Z-Cote HP1 | 1.00 |  |  |  |  |
| Mineral oil |  | 15.0 |  |  | 8.00 |
| C12–15 alkyl benzoate |  |  |  | 9.00 |  |
| Dicaprylyl ether | 10.00 |  |  |  | 7.00 |
| Butylene glycol dicaprylate/dicaprate |  |  | 2.00 | 8.00 | 4.00 |
| Dicaprylyl carbonate | 5.00 |  | 6.00 |  |  |

-continued

|  | 1 | 2 | 3 | 4 | 5 |
|---|---|---|---|---|---|
| Cocoglycerides |  | 3.00 |  |  | 5.50 |
| Dibutyl adipate |  |  |  | 4.50 |  |
| Dimethicone |  | 4.00 | 1.00 | 5.00 |  |
| Cyclomethicone | 2.00 | 25.00 |  |  | 2.00 |
| Shea butter |  |  | 3.00 |  | 4.00 |
| PVP hexadecene copolymer | 0.50 |  |  | 0.50 |  |
| Tricontanyl PVP |  |  | 0.50 | 1.00 | 0.50 |
| Ethylhexylglycerol |  | 0.30 | 1.00 |  | 0.50 |
| Glycerol | 3.00 | 7.50 |  | 7.50 | 2.50 |
| Glycine soya |  |  | 1.00 | 1.50 | 1.00 |
| MgSO₄ | 1.00 | 0.50 |  | 0.50 |  |
| MgCl₂ |  |  | 1.00 |  | 0.70 |
| Vitamin E acetate | 0.50 |  | 0.25 |  | 1.00 |
| Ubiquinone Q 10 | 0.25 | 0.10 |  |  |  |
| Panthenol |  |  | 0.50 |  |  |
| Iminodisuccinic acid | 0.30 |  |  | 0.50 |  |
| DMDM hydantoin |  | 0.60 | 0.40 | 0.20 |  |
| Methylparaben | 0.50 |  | 0.25 | 0.15 |  |
| Phenoxyethanol | 0.50 | 0.40 |  | 1.00 | 0.60 |
| Ethanol | 3.00 | 3.50 |  |  | 1.00 |
| Perfume | 0.20 |  |  | 0.20 | 0.20 |
| Water | ad 100 | ad 100 | ad 100 | ad 100 | ad 100 |

4. PIT Emulsions

|  | 1 | 2 | 3 | 4 | 5 | 6 | 7 | 8 |
|---|---|---|---|---|---|---|---|---|
| Glycerol monostearate SE | 0.50 | 2.00 | 3.00 | 5.00 |  |  | 0.50 | 4.00 |
| Glyceryl isostearate |  |  |  |  | 3.50 | 4.00 | 2.00 |  |
| Isoceteth-20 |  | 0.50 |  |  | 2.00 |  |  |  |
| Ceteareth-12 |  | 5.00 |  | 1.00 |  |  |  | 3.50 |
| Ceteareth-20 |  |  |  | 2.00 |  | 2.50 | 3.00 |  |
| PEG-100 stearate | 5.00 |  | 1.00 |  | 1.00 |  |  | 0.50 |
| Cetyl phosphate |  | 0.50 |  | 0.75 | 1.00 |  |  | 0.40 |
| Cetearyl sulfate | 0.25 |  | 0.20 |  |  |  | 0.75 |  |
| Trilaureth-4 phosphate |  | 0.10 | 0.20 |  |  | 1.00 |  |  |
| Cetyl alcohol | 2.50 | 1.00 |  | 1.50 |  | 0.50 | 1.50 |  |
| Cetyl palmitate |  |  |  | 0.50 |  | 1.00 |  |  |
| Cetyl dimethicone copolyol | 0.50 |  |  |  | 0.50 |  | 1.00 |  |
| Polyglyceryl-2 dipolyhydroxystearate |  |  |  | 0.75 | 0.25 |  |  |  |
| Diethylhexyl 2,6-naphthalate | 7.0 | 3.5 | 1.0 | 6.0 | 0.5 | 4.0 | 5.0 | 6.5 |
| Anisotriazine |  | 1.00 | 0.50 | 2.00 |  | 3.00 |  |  |
| Butylmethoxydibenzoylmethane | 1.50 |  | 1.00 |  | 5.00 |  | 3.00 |  |
| Bisimidazylate |  | 3.00 |  |  | 1.00 |  |  |  |
| Terephthalidenedicamphor-sulfonic acid |  |  | 0.50 |  |  |  | 1.00 |  |
| Drometrizole trisiloxane |  |  | 2.00 |  |  | 3.00 | 1.00 |  |
| Ethylhexyl methoxycinnamate | 8.00 | 5.00 |  | 4.50 | 5.00 | 8.00 |  |  |
| Ethylhexyl salicylate | 4.00 | 1.00 |  |  | 3.50 | 4.00 |  |  |
| Dioctylbutamidotriazone |  | 1.00 |  | 3.00 | 2.00 | 2.00 |  | 1.50 |
| Ethylhexyltriazone |  | 2.00 | 2.00 | 4.00 |  |  |  | 3.00 |
| Dimethicone diethylbenzalmalonate |  | 4.50 |  |  |  | 3.50 |  |  |
| Octocrylene |  |  |  | 5.00 |  | 8.00 |  | 7.50 |
| Phenylbenzimidazolesulfonic acid | 1.00 | 5.00 |  | 3.00 | 1.00 |  |  |  |
| C12–15 alkylbenzoate | 3.50 |  |  |  | 6.50 | 4.00 |  |  |
| Cocoglycerides |  |  | 3.00 |  | 3.00 |  | 2.50 | 3.50 |
| Dicaprylyl ether | 4.00 |  |  |  |  |  | 10.00 |  |
| Butylene glycol dicaprylate/dicaprate |  |  | 4.00 |  | 3.00 |  |  |  |
| Dicaprylyl carbonate |  |  |  | 0.50 |  |  | 2.50 | 6.00 |
| Dibutyl adipate |  |  |  | 2.50 |  | 3.00 |  | 1.00 |
| Phenyltrimethicone |  | 2.00 |  |  | 1.00 | 3.00 |  |  |
| Cyclomethicone |  |  | 3.00 |  |  |  |  | 4.00 |
| Dimethicone |  |  |  |  |  |  | 2.00 | 1.00 |
| PVP hexadecene copolymer |  |  |  |  | 1.00 | 1.50 |  |  |

-continued

|  | 1 | 2 | 3 | 4 | 5 | 6 | 7 | 8 |
|---|---|---|---|---|---|---|---|---|
| Glycerol | 10.0 | 5.00 |  | 7.50 |  |  |  |  |
| Tocopherol acetate | 1.00 |  |  | 0.75 | 0.50 |  | 1.00 |  |
| Shea butter |  | 2.00 |  |  |  |  |  | 0.50 |
| Iodopropyl butylcarbamate | 0.12 |  |  |  | 0.20 | 0.15 |  |  |
| DMDM hydantoin |  |  |  | 0.10 |  |  |  |  |
| Methylparaben |  | 0.50 | 0.25 |  | 0.45 |  |  |  |
| Phenoxyethanol | 0.50 | 0.40 |  | 1.00 |  |  |  | 1.00 |
| Octoxyglycerol |  | 0.30 |  |  | 1.00 |  |  |  |
| Ethanol |  |  |  | 2.00 |  |  | 7.50 | 4.00 |
| Trisodium EDTA |  | 0.40 |  | 0.15 |  | 0.20 |  | 0.50 |
| Iminodisuccinic acid |  | 0.25 | 0.45 |  | 1.00 | 0.12 |  |  |
| Perfume | 0.20 |  | 0.20 | 0.20 | 0.45 |  |  | 0.20 |
| Water | ad 100 | ad 100 | ad 100 | ad 100 | ad 100 | ad 100 | ad 100 | ad 100 |

That which is claimed:

1. A cosmetic or dermatological formulation comprising:
   (a) at least one UV-sensitive active ingredient,
   (b) at least one dialkyl naphthalate having the structural formula

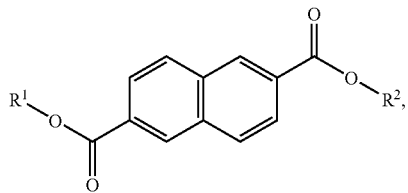

wherein $R^1$ and $R^2$, independently of one another, are selected from the group consisting of branched and unbranched alkyl groups having 6 to 24 carbon atoms, and
   (c) at least one emulsifier selected from the group consisting of phosphate emulsifiers and sulfate emulsifiers.

2. The formulation as claimed in claim 1, wherein at least one of $R^1$ and $R^2$ is a branched alkyl group having 6 to 10 carbon atoms.

3. The formulation as claimed in claim 1, wherein $R^1$ and $R^2$ are branched alkyl groups having 6 to 10 carbon atoms.

4. The formulation as claimed in claim 1, wherein the at least one dialkyl naphthalate includes diethylhexyl naphthalate.

5. The formulation as claimed in claim 1, wherein the at least one dialkyl naphthalate is present in an amount of 0.001 to 30 weight % based on the total weight of the formulation.

6. The formulation as claimed in claim 5, wherein the at least one dialkyl naphthalate is present in an amount of 0.01 to 20 weight % based on the total weight of the formulation.

7. The formulation as claimed in claim 5, wherein the at least one dialkyl naphthalate is present in an amount of 0.5 to 15 weight % based on the total weight of the formulation.

8. The formulation as claimed in claim 1, wherein the UV-sensitive active ingredient includes a dibenzoylmethane derivative.

9. The formulation as claimed in claim 8, wherein the dibenzoylmethane derivative is 4-(tert-butyl)-4'-methoxydibenzoylmethane.

10. The formulation as claimed in claim 1, wherein the at least one emulsifier has an HLB value greater than 9.

11. The formulation as claimed in claim 1, wherein the at least one emulsifier includes a phosphate emulsifier having the following structure

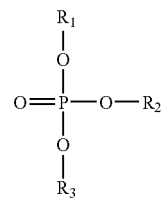

wherein $R_1$, $R_2$, and $R_3$ independently of one another are selected from the group consisting of hydrogen, branched, optionally alkoxylated, alkyl radical of 3 to 30 carbon atoms, and unbranched, optionally alkoxylated, alkyl radical of 1 to 30 carbon atoms.

12. The formulation as claimed in claim 11, wherein the phosphate emulsifier is a branched or unbranched octadecyl ester.

13. The formulation as claimed in claim 11, wherein the phosphate emulsifier is selected from the group consisting of tricetyl phosphate, cetyl phosphate, trilaureth-4 phosphate, trilaneth-4 phosphate, triceteareth-4 phosphate, trioleth-8 phosphate, trioleyl phosphate, and mixtures thereof.

14. The formulation as claimed in claim 1, wherein the at least one emulsifier includes a sulfate emulsifier.

15. The formulation as claimed in claim 14, wherein the sulfate emulsifier is sodium cetearyl sulfate.

16. The formulation as claimed in claim 1, wherein the at least one emulsifier is present in an amount of from 0.01 to 10 weight % based on the total weight of the formulation.

17. The formulation as claimed in claim 16, wherein the at least one emulsifier is present in an amount of from 0.1 to 6 weight % based on the total weight of the formulation.

18. The formulation as claimed in claim 1, wherein the at least one emulsifier and the at least one dialkyl naphthalate are present in a weight ratio of from 1:1 to 1:60.

19. The formulation as claimed in claim 18, wherein the at least one emulsifier and the at least one dialkyl naphthalate are present in a weight ratio of from 1:2 to 1:30.

20. The formulation as claimed in claim 1, further comprising at least one UV filter substance selected from the group consisting of triazines, benzotriazole, UV filters which are liquid at room temperature, organic pigments, inorganic pigments, or mixtures thereof.

21. The formulation as claimed in claim 1, further comprising at least one UV-A filter substance or broadband filter substance.

22. The formulation as claimed in claim 21, wherein the at least one UV-A filter substance or broadband filter substance is selected from the group consisting of 2,4-bis{[4-(2-ethylhexyloxy)-2-hydroxylphenyl}-6-(4-methoxyphenyl)-1,3,5-triazine, phenylene-1,4-bis(2-benzimidazyl)-3,3'-5,5'-tetrasulfonic acid bis-sodium salt, benzene-1,4-di(2-oxo-3-bornylidenemethyl-10-sulfonic acid), 2-(2H-benzotriazol-2-yl)-4-methyl-6-[2-methyl-3-[1,3,3,3-tetramethyl-1-[(trimethylsilyl)oxy]disiloxanyl]propyl]phenol, and mixtures thereof.

23. The formulation as claimed in claim 1, further comprising at least one fat-soluble active ingredient.

24. The formulation as claimed in claim 23, wherein the at least one fat-soluble active ingredient is vitamin E or a derivative thereof.

25. The formulation as claimed in claim 1, further comprising at least one water-soluble active ingredient.

26. The formulation as claimed in claim 25, wherein the at least one water-soluble active ingredient is selected from the group consisting of α-glucosylrutin, vitamin C, vitamin C derivatives, and mixtures thereof.

27. A method for moisturizing skin comprising applying to the skin a cosmetic or dermatological formulation comprising:
(a) at least one UV-sensitive active ingredient,
(b) at least one dialkyl naphthalate having the structural formula

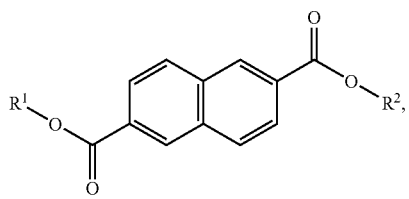

wherein $R^1$ and $R^2$, independently of one another, are selected from the group consisting of branched and unbranched alkyl groups having 6 to 24 carbon atoms, and
(c) at least one emulsifier selected from the group consisting of phosphate emulsifiers and sulfate emulsifiers.

28. A method for protecting skin against photoinduced aging comprising applying to the skin a cosmetic or dermatologic formulation comprising:
(a) at least one UV-sensitive active ingredient,
(b) at least one dialkyl naphthalate having the structural formula

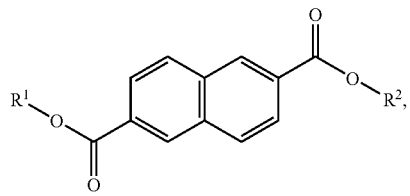

wherein $R^1$ and $R^2$, independently of one another, are selected from the group consisting of branched and unbranched alkyl groups having 6 to 24 carbon atoms, and
(c) at least one emulsifier selected from the group consisting of phosphate emulsifiers and sulfate emulsifiers.

29. A method for increasing the UV protection performance of a cosmetic or dermatological formulation comprising adding to the cosmetic or dermatological formulation at least one dialkyl naphthalate having the structural formula

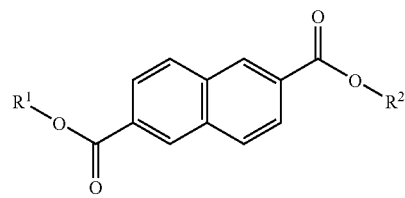

wherein $R^1$ and $R^2$ independently of one another are selected from the group consisting of branched and unbranched alkyl groups having 6 to 24 carbon atoms, and at least one emulsifier selected from the group consisting of phosphate and sulfate emulsifiers.

30. A method for stabilizing at least one cosmetic or dermatological formulation active ingredient against UV radiation-induced decomposition, wherein the method comprises adding to the cosmetic or dermatological formulation at least one dialkyl naphthalate having the structural formula

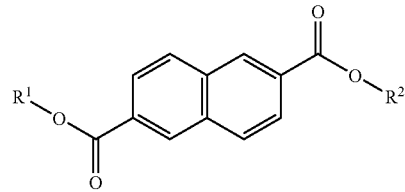

wherein $R^1$ and $R^2$ independently of one another are selected from the group consisting of branched and unbranched alkyl groups having 6 to 24 carbon atoms, and at least one emulsifier selected from the group consisting of phosphate and sulfate emulsifiers.

* * * * *